United States Patent [19]

Brand et al.

[11] Patent Number: 5,104,586
[45] Date of Patent: Apr. 14, 1992

[54] DIESTERS AND THEIR USE IN WAXES

[75] Inventors: Hans M. Brand, Ijssel; Robert P. Roggeveen, Gouda, both of Netherlands

[73] Assignee: Unilever Patent Holdings B.V., Rotterdam, Netherlands

[21] Appl. No.: 497,848

[22] Filed: Mar. 23, 1990

[30] Foreign Application Priority Data

Mar. 23, 1989 [EP] European Pat. Off. ........ 89200768.3

[51] Int. Cl.$^5$ .............................. C09F 5/8; C11C 3/10
[52] U.S. Cl. ..................................... 514/785; 554/121; 106/287.24
[58] Field of Search ......... 260/405, 410.9 R, 410.9 N; 514/785

[56] References Cited

U.S. PATENT DOCUMENTS

| | | | |
|---|---|---|---|
| 4,431,673 | 2/1984 | Goldner et al. | 424/365 |
| 4,567,037 | 1/1986 | Ciandelli | 260/405 |
| 4,867,965 | 9/1989 | Ciandelli | 260/405 |

FOREIGN PATENT DOCUMENTS 0013755 8/1980 European Pat. Off.
0182355 5/1986 European Pat. Off.

OTHER PUBLICATIONS

Brand et al., Seifen-Ole-Fette-Wachse, vol. 114, pp. 547–552 (1988).

Primary Examiner—Jose G. Dees
Assistant Examiner—Deborah D. Carr
Attorney, Agent, or Firm—Cushman, Darby & Cushman

[57] ABSTRACT

The invention provides a diester of the formula $CH_3(CH_2)_5CH(OCOR^1)(CH_2)_{10}COOR^2$, in which $R^1$ is a saturated, branched chain hydrocarbon radical having 15 to 21 carbon atoms and $R^2$ is a saturated, branched chain hydrocarbon radical having 8 to 22 carbon atoms. Preferably $R^1$ is a methyl branched chain radical and contains 17 carbon atoms and statistically between 0.5 and 1.0 methyl side-chain per molecule, whereas $R^2$ contains 18 to 22 carbon atoms with a $C_1$–$C_8$, preferably $C_1$ side-chain. The invention also provides a wax composition comprising a diester defined above optionally together with a hydrocarbon oil ($C_{16}$–$C_{32}$ and saturated), a $C_{12}$–$C_{22}$ optionally branched chain fatty acid and a monoester derived from a $C_{18}$ to $C_{22}$ fatty acid and a $C_{12}$ to $C_{22}$ alcohol. Furthermore the invention provides cosmetic preparations containing a wax composition as defined above.

9 Claims, No Drawings

DIESTERS AND THEIR USE IN WAXES

The invention relates to novel diesters and their use in waxes, more in particular in high performance waxes with beeswax-like properties. Beeswax is a natural wax, which because of its special properties is often used for cosmetic purposes and in medicine. It is self-emulsifying after the addition of alkali and has an emollient effect on the skin giving a film permeable for moisture (ie. water vapour) and gas.

Several attempts have been made to prepare wax compositions having beeswax-like properties which can serve as replacements or extenders for beeswax, however, no satisfactory composition has so far been developed. Components which have been suggested for such wax compositions comprise: fatty acids, triglycerides, higher monoesters, oxidized microcrystalline wax, synthetic alcohols, Fischer-Tropsch wax etc.

More specifically EP-A-13 755 (Henkel) discloses a beeswax substitute comprising triglycerides of alpha-branched long chain carboxylic acids (so-called Guerbet acids), paraffin oil, fatty acid etc. EP-A-182 355 (Revlon) discloses certain esters of 12-hydroxystearic acid which have been esterified inter alia with unsaturated (1 to 3 double bonds), natural, straight chain fatty acids like oleic acid, linoleic acid, linolenic acid and a $C_5$ to $C_{22}$ alcohol like octanol, isocetanol or isostearyl alcohol. These esters were used in cosmetic, household and pharmaceutical preparations together with other components such as mineral oil, fatty acids, glycerides etc. Furthermore US-A-4 431 673 (Revlon) discloses cosmetic preparations comprising a long chain alkyl ester of a long chain aliphatic alcohol such as 2-octyl-dodecyl-12-stearoyloxystearate. Finally there is Seifen Oele Fette Wachse Volume 114 (1988) pp 547-552 summarizing analytical work on beeswax describing that the main fractions are: free fatty acids, paraffinic hydrocarbons, straight chain, simple esters and complex esters which are di-, tri- and higher esters derived from 15-hydroxypalmitic acid and which esters often still have free carboxylic- or hydroxyl groups in the molecule. It is especially this group of complex esters which is held responsible for imparting moisture and oxygen permeability to beeswax. It is also clear from this article that despite a recent decline in the production of beeswax and great endeavours made no suitable replacement for beeswax has been commercially available so far.

It is an object of the present invention to provide a suitable replacement for beeswax which is liquid at room temperature and which is of a good colour, is stable to oxidation and has the desirable qualities of moisture and oxygen permeability.

The present invention now provides a diester of the formula $CH_3(CH_2)_5CH(OCOR^1)(CH_2)_{10}COOR^2$, in which $R^1$ is a saturated, branched chain hydrocarbon radical having 15 to 21 carbon atoms and $R^2$ is a saturated, branched chain hydrocarbon radical having 8 to 22 carbon atoms.

Diesters of this type are valuable constituents of high performance waxes as they can impart to a wax film properties like air and water permeability in combination with excellent emollient properties. They are also of a good colour, are stable to oxidation and exhibit low melting points, eg. below 0° C. The above diesters are derived from 12-hydroxystearic acid, a saturated, branched chain $C_{16}$ to $C_{22}$ carboxylic acid and a $C_8$ to $C_{22}$ saturated, branched chain alcohol. The diesters can conveniently be prepared from the above three classes of compounds by esterification reactions. Suitable carboxylic acid starting materials are e.g. isopalmitic acid, isostearic acid, and isobehenic acid which acids can be obtained by reacting palmitoleic acid, oleic acid, erucic acid or mixtures thereof using a clay catalyst at temperatures of 240° to 280° C. for several hours under steam pressure, stripping off the partly isomerized, unpolymerized fraction which is then hydrogenated and (solvent) fractionated to yield a liquid, mixture of methyl branched chain saturated $C_{16}$ to $C_{22}$ fatty acids containing usually 0.5 to 1.0, preferably 0.6 to 0.9 methyl side-chain per molecule. Suitable alcohols are saturated branched chain $C_8$-$C_{22}$ alcohols as e.g. 2-ethylhexanol, isocetanol, Guerbet alcohols like 4-and/or 5-octyl-dodecanol, isopalmityl alcohol, isostearyl alcohol, isobehenyl alcohol etc. The latter three alcohols can be prepared by reduction of the corresponding branched chain carboxylic acids. 12-Hydroxystearic acid can technically be obtained by hydrogenation of ricinoleic acid. Primary alcohols are preferred.

Preferably the diester according to the present invention satisfies the above formula in which $R^1$ is a methyl branched chain radical eg. derived from isopalmitic acid, isostearic acid or isobehenic acid. More preferably $R^1$ contains 17 carbon atoms and statistically between 0.5 and 1.0, preferably between 0.6 and 0.9 methyl side-chain per molecule and is the hydrocarbyl group of technical isostearic acid. A diester in which $R^2$ contains 18 to 22 carbon atoms with a $C_1$-$C_8$ contains 18 to 22 carbon atoms side-chain is preferred. More preferred is a diester in which the side-chain is a methyl group (from isopalmityl-, isostearyl- or isobehenyl alcohol). Diesters with excellent properties in waxes are those in which both $R^1$ and $R^2$ are both radicals derived from isopalmitic, isostearic or isobehenic acid or alcohol with particular emphasis on those derived from isostearic acid. The diesters according to the present invention can be prepared by various methods known per se e.g. from 12-hydroxystearic acid, a suitable branched chain acid and alcohol or functional derivatives thereof by esterification, inter-esterification or re-esterification techniques known in the art. One particularly attractive synthesis uses hydrogenated ricinoleic acid glycerides rich in glycerides of 12-hydroxystearic acid (hydrogenated castor oil or a fraction thereof) and esterifies the free hydroxyl groups thereof with a suitable branched chain acid using a tetraalkyl-titanium or zirconium catalyst. Subsequently partial hydrolysis is effected by treatment with a weak alkaline aqueous solution such as aqueous sodium acetate, after which the glycerol is washed out. Then the reaction mixture is subjected to distillation and the (partial) acidester so obtained is esterified with a suitable branched chain alcohol whilst eliminating water of reaction. The diester can then be further purified e.g. by fractional distillation under vacuum.

The diesters according to the present invention are valuable ingredients in wax compositions and the invention provides wax compositions comprising such a diester in conjunction with other wax components. Preferably the wax composition further comprises a hydrocarbon oil ($C_{16}$-$C_{32}$ and saturated), a $C_{12}$-$C_{22}$ preferably branched chain fatty acid and a monoester derived from a saturated, preferably branched chain, $C_{18}$ to $C_{22}$ fatty acid and a $C_{12}$ to $C_{22}$ branched chain alcohol. Especially with diesters in which at least one $C_{12}$ to $C_{22}$ branched chain compound is derived from isostearic acid favourable properties are obtained in waxes.

The invention also provides a wax composition which contains:

- 5 to 10 % (w.w.) of diester according to the general formula specified above,
- 55 to 80 % (w.w.) of monoester as defined above,
- 5 to 20 % (w.w.) of hydrocarbon oil as defined above,
- 10 to 20 % (w.w.) of branched chain fatty acid as defined above.

Preferably the above composition is so compounded that the blend shows an acid value of 15 to 35 (most preferably from 17 to 22), an ester value of 65 to 85 (most preferably from 70 to 80) and an iodine value below 2.

Wax compositions described above are self-emulsifying upon addition of alkali or an alkanolamine and have good permeability for water vapour and air combined with good emollient functions so that they are valuable ingredients for cosmetic preparations and the invention thus also provides cosmetic and pharmaceutical preparations containing a wax composition as described above. Cosmetic and wax compositions described above combined excellent softening and emolliency on the skin and leave a film which is permeable for water vapour and gas so that the skin with such a film continues to "breathe" and no bubbling of the film occurs. Also the diesters according to the present invention show excellent oxidative stability due to complete saturation in combination with a remarkable low melting point necessary for good emolliency, good absorbency and a good afterfeel. Usually the cosmetic preparations contain from 2 to 50, preferably from 6 to 12 % (w.w.) of wax composition according to the present invention.

The invention is illustrated by the following examples.

EXAMPLE 1

First step

Esterification of 12-hydroxystearic acid (A.V.=185; OH.V.=153; S.V.=187; I.V.=1.2) with isostearyl alcohol (A.V.=below 0.1; S.V.=below 1.0; OH.V.=204; I.V.=1.0; colour below 20 APHA) and isostearic acid (A.V.=194; S.V.=196; I.V.=1.3 ; colour 50-60 APHA). Starting materials:

| | |
|---|---|
| 12-hydroxystearic acid | 55% weight % |
| Isostearyl alcohol | 42% weight % |
| p.toluenesulfonic acid (TSA) | 0.16 weight % |
| Hypophosphorous acid | 0.08 weight % |
| NaOH-solution (10%) | 1.2 vol % |
| Activated carbon | 0.6 weight % |
| Fullers earth | 0.8 weight % |

The mixture of 12-hydroxystearic acid, isostearyl alcohol, p-toluenesulfonic acid and hypophosphorous acid was heated to 120° C. Esterification took place for six hours. After two hours of the esterification time, vacuum was applied using an oilpump (about 400 Pa). When the acid value (A.V.) was below 2, the product was refined by adding the NaOH-solution at a temperature of 80° C. After one hour agitation activated carbon and Fullers earth were added. Drying took 1.5 hours (200 Pa). Filtration was done with filter aid at a temperature of 60°-70° C.

Properties of the diester obtained (A.V.=0.1; S.V.=101; OH.V.=81; I.V=1.0; colour 300–400 APHA).

Second step

| Raw materials: | |
|---|---|
| Isostearyl-12-hydroxystearate | 65.5 weight % |
| Isostearic acid | 22.7 weight % |
| Stannous-oxalate | 0.04 weight % |
| Phosphoric acid (75%) | 0.13 weight % |
| Activated carbon | 10.7 weight % |
| Fullers earth | 0.95 weight % |

The mixture of isostearyl-12-hydroxy-stearate, isostearic acid and stannous-oxalate was heated to 230° C. Esterification took place for five hours (2.7 KPa). After five hours the acid value was found to be approximately 16. After another two hours of reaction at a higher temperature 245° C., 2.7 Kpa) the acid value had hardly changed and was found to be approximately 13. Esterification was stopped by adding the phosphoric acid at a temperature of 90° C. The mixture was stirred for two hours (100 KPa). After adding the activated carbon and Fullers earth the solution was dried for 1.5 hours at a temperature of 90° C. (at 200 Pa). Filtration was done with Supercel at a temperature of 70° C. Properties of the diester obtained are A.V.=11.7 S.V.=117; OH.V=9; I.V=3; viscosity 40° C., 65.4 mm$^2$/s. Glc. $C_{18}$6%; $C_{36}$29%; $C_{54}$ 65%; $C_{72}$19%. Further purification of the diester was effected by fractional distillation under vacuum recovering a predominantly $C_{54}$–$C_{72}$ fraction followed by 0 HPLC to recover the pure diester.

EXAMPLE 2

Esterification of 12-hydroxystearic acid with isostearic acid and isostearyl alcohol.

First step

| Raw materials: | |
|---|---|
| 12-hydroxystearic acid | 1027.0 g |
| Isostearic acid 3505 | 982.1 g |
| p.toluenesulfonic acid | 3.21 g |
| Hypophosphorous acid | 1.60 g |

The mixture of 12-hydroxystearic acid, isostearic acid, p.TSA and hypophosphorous was heated to 120° C. Esterification took place for 5.5 hours (200 Pa). After the first reaction step it was not necessary to refine or filtrate the product because of the reuse of the catalyst in the second step.

Second step

| Raw materials: | |
|---|---|
| 12-isostearylstearic acid | 1810 g |
| Isostearyl alcohol | 1147.8 g |
| NaOH-solution (33%) | 3.0 g |
| Activated carbon | 17.7 g |
| Fullers earth | 23.6 g |
| Decalite (Filter aid) | 10 g |
| Catalyst | from first step |

The mixture of 12-isostearylstearic acid and isostearyl alcohol was heated to 120° C. Esterification took place for 10.5 hours (200 Pa). When the acid value was below 2, the NaOH-solution was added at a temperature of 90° C. After half an hour agitation activated carbon, Decalite and Fullers earth were added. Drying took 1.5 hours (half an hour at 100 KPa and one hour at 250 Pa). Filtration was done with filter aid at a temperature of 60° C. Properties of the diester obtained are: A.V.=1.2; S.V.=107; I.V.=1.1; OH.V.=14; Viscosity 40° C. 52.3 mm2/s and a pour point −34° C. Glc. 6% $C_{18}$, 44% $C_{36}$, 51% $C_{54}$, 21% $C_{72}$. Further purification of the diester was effected by molecular distillation.

EXAMPLE 3

A wax composition was prepared by mixing the following ingredients:
- 15% (w.w.) Paraffin oil ($C_{16}$–$C_{32}$ saturated)
- 10% (w.w.) Isostearic acid (as in Example I)
- 65% (w.w.) Isostearyl isostearate (A.V.=0.1; S.V.=106; I.V.=1.8, Colour 80 APHA)
- 10% (w.w.) Isostearyl-12-isostearoyl stearate obtained according to Example 1.

The liquid wax so obtained had an A.V.=20.2; S.V.=101, and a melting point of below 20° C. and did not show any crystallization when kept at 4° C. for 6 hours.

EXAMPLE 4

The wax obtained according to the previous example was emulsified by preparing an oil phase consisting of 11 parts of the wax according to Example 3 and adding 40 parts of paraffine oil (also described in Example 3) and preparing a water phase consisting of 0.5 part triethanolamine and 48.5 parts of demineralized water. A cold cream base was thus prepared by homogenizing the quantities oil phase and water phase mentioned above with a high speed mixer (10 seconds 3,000 rpm).

EXAMPLE 5

A wax preparation we prepared by heating and mixing the following ingredients:
- 14% (w.w.) of paraffin oil as in Example 3
- 9% (w.w.) of isostearic acid as in Example 1
- 63% (w.w.) Cetearyl stearate
- 10% (w.w.) Isostearyl-12-isostearoyl stearate
- 4% (w.w.) Hexaglyceryl dioleate (hexaglycerol esterified with 2 moles of oleic acid)

The wax so obtained had a higher melting point than the wax of Example 3 and remained substantially amorphous upon storage.

EXAMPLE 6

The wax prepared according to Example 5 was emulsified by first preparing an oily phase consisting of
- 17.5 parts (w.w) of the wax of Example 2
- 2.5 parts (w.w) of ozokerite
- 1 part (w.w.) of paraffin (m.p. 50°–52° C.)
- 1 part (w.w.) of lanoline
- 52 parts (w.w.) of paraffin oil ($C_{16}$–$C_{32}$)

which oil phase was emulsified at 65° C. in a water phase consisting of 25.5 parts of water and 0.75 part of borax at 3000 rpm for 5 seconds. The cream so obtained showed good emolliency, a pleasant skinfeel and was easy to spread. Upon perspiring no bubbles occurred.

EXAMPLE 7

A thixotropic day cream was prepared by heating and mixing an oil phase consisting of:
- 9 parts (w.w.) of wax composition of Example 5
- 5 parts (w.w.) of paraffin oil of Example 3
- 2 parts (w.w.) of lanolin
- 2 parts (w.w.) of sorbitan monostearate
- 1 part (w.w.) of castor oil with a water phase consisting of
- 78 parts (w.w.) of water
- 1 part (w.w.) of glycerol
- 1 part (w.w.) of POE-20 sorbitan monostearate
- 0.2 part (w.w.) of triethanolamine.

The thixotropic cream so obtained had a good skinfeel. The lipid film on the skin was permeable for air and water vapour and no bubble formation of the lipid film was observed.

EXAMPLE 8

A skin milk was prepared by heating and mixing
- 6 parts (w.w.) wax of Example 3
- 2.2 parts (w.w.) ceteareth-6
- 2.2 parts (w.w.) ceteareth-25
- 1 part (w.w.) ceteareth alcohol
- 2 parts (w.w.) almond oil
- 2 parts (w.w.) of avacado oil
- 0.5 parts (w.w.) acetylated lanolin as the oil phase with a water phase consisting of 2 parts of glycerol, 1 part (w.w.) propylene glycol, 0.5 part (w.w.) of p.hydroxybenzoic acid and 80.6 parts (w.w.) of demineralized water.

We claim:

1. A diester of the formula $CH_3(CH_2)_5CH(OCOR^1)(CH_2)_{10}COOR^2$, characterized in that $R^1$ is a saturated, branched chain hydrocarbon radical having 15 to 21 carbon atoms and $R^2$ is a saturated, branched chain hydrocarbon radical having 8 to 22 carbon atoms.

2. A diester according to claim 1 characterized in that $R^1$ contains 17 carbon atoms and statistically between 0.5 and 1.0 methyl side-chain per molecule.

3. A diester according to claim-I characterized in that $R^2$ contains 18 to 22 carbon atoms with $C_1$–$C_8$ side-chain.

4. A diester according to claim 1 in which both $R^1$ and $R^2$ are radicals derived from isostearic acid.

5. A wax composition characterized in that it comprises a diester according to any of the preceding claims.

6. A wax composition according to claim 5 characterized in that it further comprises a hydrocarbon oil ($C_{16}$–$C_{32}$ and saturated), a $C_{12}$–$C_{22}$ fatty acid and a monoester derived from a saturated, $C_{18}$ to $C_{22}$ fatty acid and a $C_{12}$ to $C_{22}$ branched chain, alcohol.

7. A wax composition according to claim 6 characterized in that the fatty acid and/or the monoester is derived from isostearic acid.

8. A wax composition according to claim 6 characterized in that it contains:
- 5 to 10 % (w.w.) of the diester
- 55 to 80 % (w.w.) of the monoester
- 5 to 20 % (w.w.) of the hydrocarbon oil
- 10 to 20 % (w.w.) of the fatty acid 9. A cosmetic preparation characterized in that it contains from 2 to 50% (w.w.) of a wax composition according to claim 6.

* * * * *